US00PP19057P2

(12) United States Plant Patent
Fraser

(10) Patent No.: US PP19,057 P2
(45) Date of Patent: Jul. 29, 2008

(54) ***COPROSMA* PLANT NAMED 'GOLDEN GLOW'**

(50) Latin Name: *Coprosma*
Varietal Denomination: Golden Glow

(76) Inventor: Peter Fraser, P.O. Box 29, Kihikihi Waikato (NZ)

( * ) Notice: Subject to any disclaimer, the term of this patent is extended or adjusted under 35 U.S.C. 154(b) by 0 days.

(21) Appl. No.: 11/648,351

(22) Filed: Dec. 29, 2006

(51) Int. Cl.
*A01H 5/00* (2006.01)

(52) U.S. Cl. ..... Plt./263.1

(58) Field of Classification Search ..... Plt./263.1
See application file for complete search history.

(56) References Cited

PUBLICATIONS

UPOVROM Citation for 'Corprosma' as per NZ PBR SHM205; Jun. 14, 2005.*

* cited by examiner

*Primary Examiner*—Kent L Bell

(57) ABSTRACT

A new cultivar of *Coprosma* plant named 'Golden Glow' that is characterized by an upright habit and leaves that are green when young then turn to yellow and then to orange when mature.

1 Drawing Sheet

Botanical Classification: *Coprosma*.
Variety Denomination: 'Golden Glow'.

BACKGROUND OF THE INVENTION

The present invention relates to a new and distinct cultivar of *Coprosma* plant botanically known as *Coprosma* and hereinafter referred to by the cultivar name 'Golden Glow'.

The new cultivar was discovered by the inventor in a cultivated area of Waikato, New Zealand in 2004. 'Golden Glow' was discovered as a naturally occurring branch mutation of *Coprosma* 'Evening Glow' (not patented).

Asexual reproduction by tip cuttings of the new cultivar 'Golden Glow' was first performed in 2004 in Waikato, New Zealand. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Coprosma* cultivar 'Golden Glow'.

1. Coprosma 'Golden Glow' exhibits an upright habit.
2. Coprosma 'Golden Glow' exhibits leaves that are lime green when young, then turn yellow, then orange when mature.

The closest comparison cultivar is the parent plant *Coprosma* 'Evening Glow'. The new cultivar 'Golden Glow' is distinguishable from 'Evening Glow' by the following characteristics:

1. 'Golden Glow' has leaves that are lime green when young, then turn yellow, then orange. The leaves of 'Evening Glow' are green when young, then turn orange.
2. 'Golden Glow' has a more upright habit. 'Evening Glow' has a more spreading habit.

BRIEF DESCRIPTION OF THE DRAWING

The accompanying photograph illustrates the distinguishing traits of *Coprosma* 'Golden Glow'. The plant in the photograph shows an overall view of a 12 month old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Coprosma* cultivar named 'Golden Glow'. Data was collected in Waikato, New Zealand from 12 month old outdoor grown plants in 2.5 liter containters. The time of year was Winter and the average temperature range was 5 to 15 degrees Centigrade during the day and 2 to 8 degrees Centigrade at night. No photoperiodic treatments or growth retardants were used. Color determinations are in accordance with the Royal Horticultural Society Colour Chart 2001 edition, except where general color terms of ordinary dictionary significance are used. The growing requirements are similar to the species. 'Golden Glow' has not been tested under all possible conditions and phenotype differences may be observed with variations in environmental, climatic, and cultural conditions, however, without any variance in genotype.

Botanical classification: *Coprosma* 'Golden Glow'.
Use: Ornamental perennial.
Parentage: 'Golden Glow' is a naturally occurring branch mutation of *Coprosma* 'Evening Glow'.
Vigor: Moderate.
Growth rate: Moderate.
Growth habit: Freely branching, dense, bushy habit.
Plant shape: Broad upright inverted triangle.
Suitable container size: 2.5 liter container.
Height: Average 1.5 m in height.
Width: Average 1.5 m in width.

Hardiness: Tolerant to −3 degrees Centigrade.
Propagation: Tip cuttings.
Time to initiate roots: Approximately 21 days in the Summer and 28 days in the Winter.
Time to produce a rooted cutting: Approximately 40 days in the Summer and 55 days in the Winter.
Root system: Fine and fibrous.
Lateral Branches:
*Quantity.*—Approximately 20.
*Length.*—Average 15 cm.
*Diameter.*—Average 3 mm.
*Internode length.*—10 mm.
*Color.*—Young 143A, mature 197B.
*Strength.*—Strong.
*Pinching.*—No.
Foliage:
*Texture.*—Smooth, glossy.
*Leaf arrangement.*—Opposite.
*Leaf attachment.*—Sessile.
*Compound of single.*—Single.
*Leaf shape.*—Obovate.
*Leaf apex.*—Obtuse.
*Leaf base.*—Rounded.
*Leaf length.*—Average 2.5 cm in length.
*Leaf width.*—1.0 cm in width.
*Pubescence.*—Absent.
*Leaf margin.*—Entire, unevenly recurved, slightly wavy.
*Vein pattern.*—Pinnate.
*Young leaf color* (*upper surface*).—154B.
*Young leaf color* (*lower surface*).—154B.
*Mature leaf color* (*upper surface*).—34A with blotches toward margin 143A.
*Mature leaf color* (*lower surface*).—34A with blotches toward margin 143A.
*Durability of foliage to stress.*—Moderate to high.
Flowers: Flowers have not been observed.
Disease and insect resistance: Plants of the new *Coprosma* have not been observed for disease or insect resistance.

It is claimed:

1. A new and distinct variety of *Coprosma* plant named 'Golden Glow' as described and illustrated.

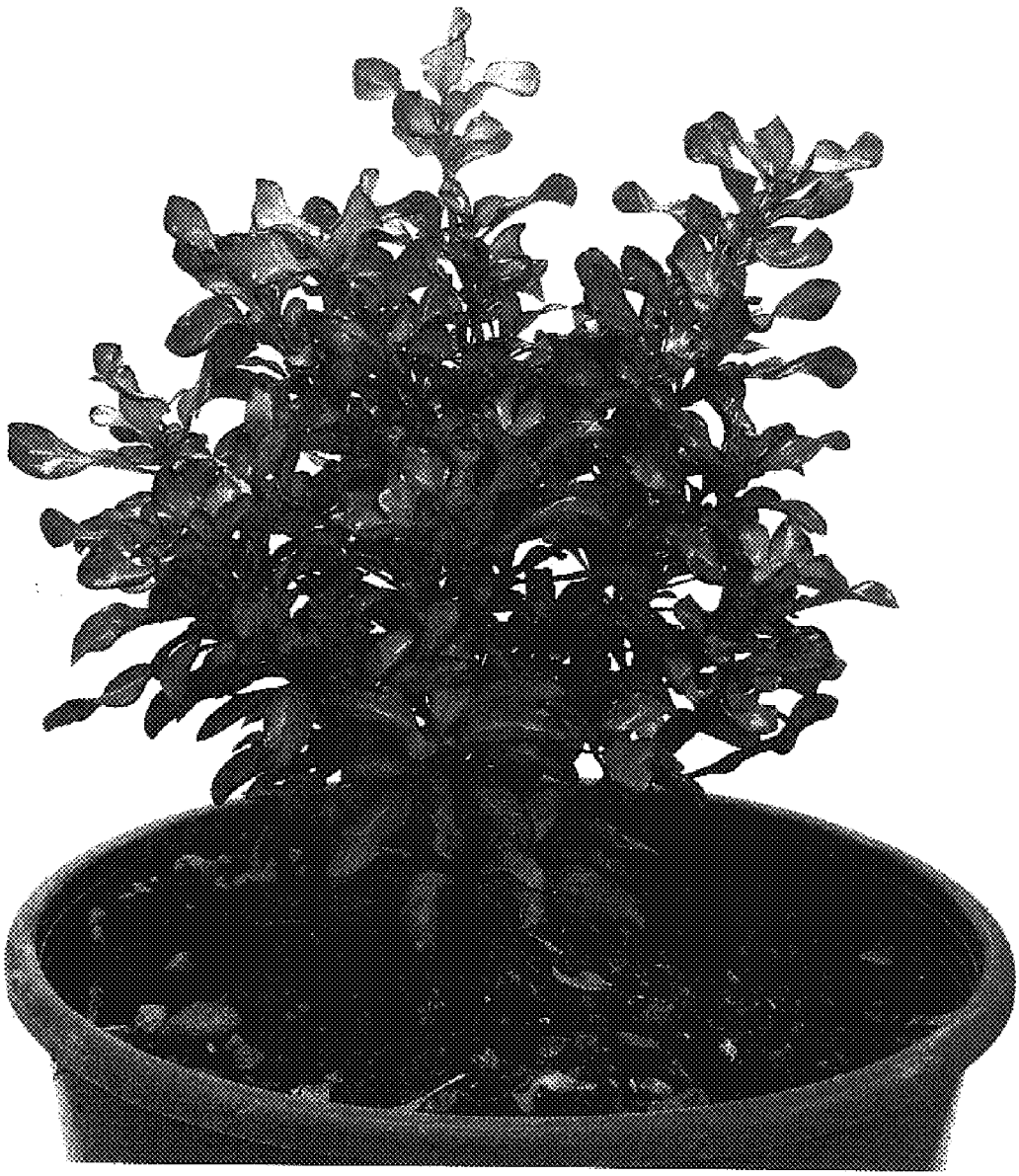

* * * * *